United States Patent
Nagamoto et al.

(10) Patent No.: US 11,583,703 B2
(45) Date of Patent: Feb. 21, 2023

(54) PARTICLE BEAM THERAPY SYSTEM, PARTICLE BEAM THERAPY SYSTEM CONSTRUCTION METHOD, AND PARTICLE BEAM THERAPY APPARATUS

(71) Applicants: KABUSHIKI KAISHA TOSHIBA, Tokyo (JP); TOSHIBA ENERGY SYSTEMS & SOLUTIONS CORPORATION, Kawasaki (JP)

(72) Inventors: Yoshifumi Nagamoto, Yokohama (JP); Yoshiharu Kanai, Yokohama (JP); Takashi Yazawa, Ota (JP)

(73) Assignees: KABUSHIKI KAISHA TOSHIBA, Tokyo (JP); TOSHIBA ENERGY SYSTEMS & SOLUTIONS CORPORATION, Kawasaki (JP)

( * ) Notice: Subject to any disclaimer, the term of this patent is extended or adjusted under 35 U.S.C. 154(b) by 63 days.

(21) Appl. No.: 17/037,839

(22) Filed: Sep. 30, 2020

(65) Prior Publication Data
US 2021/0008393 A1   Jan. 14, 2021

Related U.S. Application Data

(63) Continuation of application No. PCT/JP2019/006985, filed on Feb. 25, 2019.

(30) Foreign Application Priority Data

Apr. 23, 2018 (JP) .............................. JP2018-082245

(51) Int. Cl.
A61N 5/10 (2006.01)
G21F 7/005 (2006.01)

(52) U.S. Cl.
CPC ......... A61N 5/1079 (2013.01); A61N 5/1081 (2013.01); G21F 7/005 (2013.01);
(Continued)

(58) Field of Classification Search
CPC ...... A61N 5/10; A61N 5/1077; A61N 5/1079; A61N 5/1081; A61N 5/1082;
(Continued)

(56) References Cited

U.S. PATENT DOCUMENTS 5,851,182 A * 12/1998 Sahadevan ........... A61N 5/1049
378/65
6,894,300 B2 * 5/2005 Reimoser ................. G21K 5/04
250/517.1
(Continued)

FOREIGN PATENT DOCUMENTS

CN 102188776 A 9/2011
CN 104338243 A 2/2015
(Continued)

OTHER PUBLICATIONS

International Search Report dated Apr. 16, 2019 in PCT/JP2019/066985 filed on Feb. 25, 2019, 2 pages.

Primary Examiner — Thomas R Artman
(74) Attorney, Agent, or Firm — Oblon, McClelland, Maier & Neustadt, L.L.P.

(57) ABSTRACT

According to one embodiment, a particle beam therapy system comprising: a circular accelerator configured to accelerate charged particles; a beam transportation line configured to lead the charged particles accelerated by the circular accelerator to an irradiation room; a shielding wall that is disposed around a radiation controlled area and shields radiation to be generated from the circular accelerator and the beam transportation line, the radiation controlled area being an area where the circular accelerator and the beam transportation line are disposed; a specific portion that is provided at a position that separates the radiation controlled area from outside of the shielding wall and can form an additional opening portion of the irradiation room; and a (Continued)

blocking portion configured to close the specific portion and shield radiation passing through the specific portion.

14 Claims, 11 Drawing Sheets

(52) U.S. Cl.
CPC ............. *A61N 2005/1087* (2013.01); *A61N 2005/1094* (2013.01)

(58) Field of Classification Search
CPC .... A61N 2005/1092; A61N 2005/1094; A61B 6/4092; A61B 6/44; A61B 6/4411; A61B 2560/04; A61B 2560/0443; F16L 3/02; F16L 3/04; F16L 3/08; F16L 3/26; F16L 5/00; F16L 9/22; F16L 23/006; F16L 23/12; F16L 41/02; F16L 2201/40
See application file for complete search history.

(56) References Cited

U.S. PATENT DOCUMENTS

| | | | |
|---|---|---|---|
| 7,319,231 B2* | 1/2008 | Moriyama | A61N 5/10 378/65 |
| 10,556,131 B2 | 2/2020 | Hori et al. | |
| 11,389,671 B2* | 7/2022 | Aono | A61N 5/1075 |
| 2004/0118081 A1 | 6/2004 | Reimoser et al. | |
| 2004/0183033 A1* | 9/2004 | Moriyama | A61N 5/1079 250/398 |
| 2011/0220809 A1 | 9/2011 | Yajima et al. | |
| 2012/0119106 A1 | 5/2012 | Uno | |
| 2013/0048883 A1* | 2/2013 | Simon | A61N 5/1048 250/492.3 |
| 2016/0074676 A1 | 3/2016 | Yajima et al. | |
| 2018/0064957 A1 | 3/2018 | Hori et al. | |
| 2018/0214715 A1 | 8/2018 | Takayama et al. | |
| 2019/0269941 A1* | 9/2019 | Aono | A61N 5/1065 |
| 2020/0094077 A1* | 3/2020 | Nishiuchi | G21K 1/00 |
| 2021/0008393 A1* | 1/2021 | Nagamoto | G21F 7/005 |

FOREIGN PATENT DOCUMENTS

| | | |
|---|---|---|
| CN | 106924891 A | 7/2017 |
| CN | 107596579 A | 1/2018 |
| EP | 2 316 527 A1 | 5/2011 |
| EP | 2 364 750 A1 | 9/2011 |
| JP | 2011-182987 A | 9/2011 |
| JP | 2012-100915 A | 5/2012 |
| JP | 2017-029235 A | 2/2017 |
| JP | 2017-80487 A | 5/2017 |
| JP | 2018-038628 A | 3/2018 |
| JP | 2019-150295 A | 9/2019 |
| KR | 10-0622935 B1 | 9/2006 |
| KR | 10-2011-0102239 A | 9/2011 |

* cited by examiner

PARTICLE BEAM THERAPY SYSTEM, PARTICLE BEAM THERAPY SYSTEM CONSTRUCTION METHOD, AND PARTICLE BEAM THERAPY APPARATUS

CROSS-REFERENCE TO RELATED APPLICATIONS

This application is a Continuation Application of No. PCT/JP2019/006985, filed on Feb. 25, 2019, and the PCT application is based upon and claims the benefit of priority from Japanese Patent Application No. 2018-082245, filed on Apr. 23, 2018, the entire contents of which are incorporated herein by reference.

TECHNICAL FIELD

Embodiments of the present invention relate to a particle beam therapy system, a particle beam therapy system construction method, and a particle beam therapy apparatus.

BACKGROUND

In a conventional particle beam therapy system, therapy is performed by irradiating a lesion portion (cancer) of a patient with a particle beam. In the case of updating the system of such a particle beam therapy system, the system is updated by establishing a new treatment room and alternately operating this new treatment room and the existing treatment room while the treatment is being continued.

PRIOR ART DOCUMENT

Patent Document

[Patent Document 1] JP 2018-038628 A

SUMMARY

Problems to be Solved by Invention

In the particle beam therapy system, a thick shielding wall for blocking radioactive rays is provided around a radiation controlled area where the accelerator is disposed. In the case of updating the system except in an unprepared treatment room that is provided in the building in advance, part of this shielding wall must be demolished and a path for extending the accelerator must be constructed. Thus, there is a problem that it takes a long time to demolish the shielding wall and this causes extended interruption period of treatment and reduction in operating rate of the system.

In view of the above-described circumstances, an object of embodiments of the present invention is to provide technology for constructing a particle beam therapy system that can improve its operating rate by shortening the interruption period of treatment during construction.

DETAILED DESCRIPTION

In one embodiment of the present invention, a particle beam therapy system comprising:
- a circular accelerator configured to accelerate charged particles;
- a beam transportation line configured to lead the charged particles accelerated by the circular accelerator to an irradiation room;
- a shielding wall that is disposed around a radiation controlled area and shields radiation to be generated from the circular accelerator and the beam transportation line, the radiation controlled area being an area where the circular accelerator and the beam transportation line are disposed;
- a specific portion that is provided at a position that separates the radiation controlled area from outside of the shielding wall and can form an additional opening portion of the irradiation room; and
- a blocking portion configured to close the specific portion and shield radiation passing through the specific portion.

(First Embodiment)

Hereinbelow, embodiments will be described by referring to the accompanying drawings. First, a description will be given of a particle beam therapy apparatus according to the first embodiment by referring to FIG. 1 to FIG. 7. The reference sign 1 in FIG. 1 indicates the particle beam therapy apparatus. In this particle beam therapy system 1, therapy is performed by irradiating a lesion tissue (cancer) of a patient as a subject with a particle beam such as carbon ions.

Radiation therapy technology using the particle beam therapy system 1 is also called heavy-particle-beam cancer therapy technology. In this technology, cancer lesions (affected areas) can be irradiated with carbon ions with pinpoint accuracy and damage to normal cells can be minimized while cancer lesions are being damaged. A particle beam is defined as heavier than an electron among radiation and includes a proton beam and a heavy particle beam. Of these, the heavy particle beam is defined as heavier than a helium atom.

As compared with conventional cancer treatment using X-rays, gamma rays, or proton rays, cancer treatment using heavy ion beams has a higher ability to kill cancer lesions and has the characteristic that the radiation dose is weak on the surface of the patient's body and reaches a peak at the cancer lesions. Thus, it can reduce the number of irradiation and side effects and can shorten the treatment period.

Figure 1:
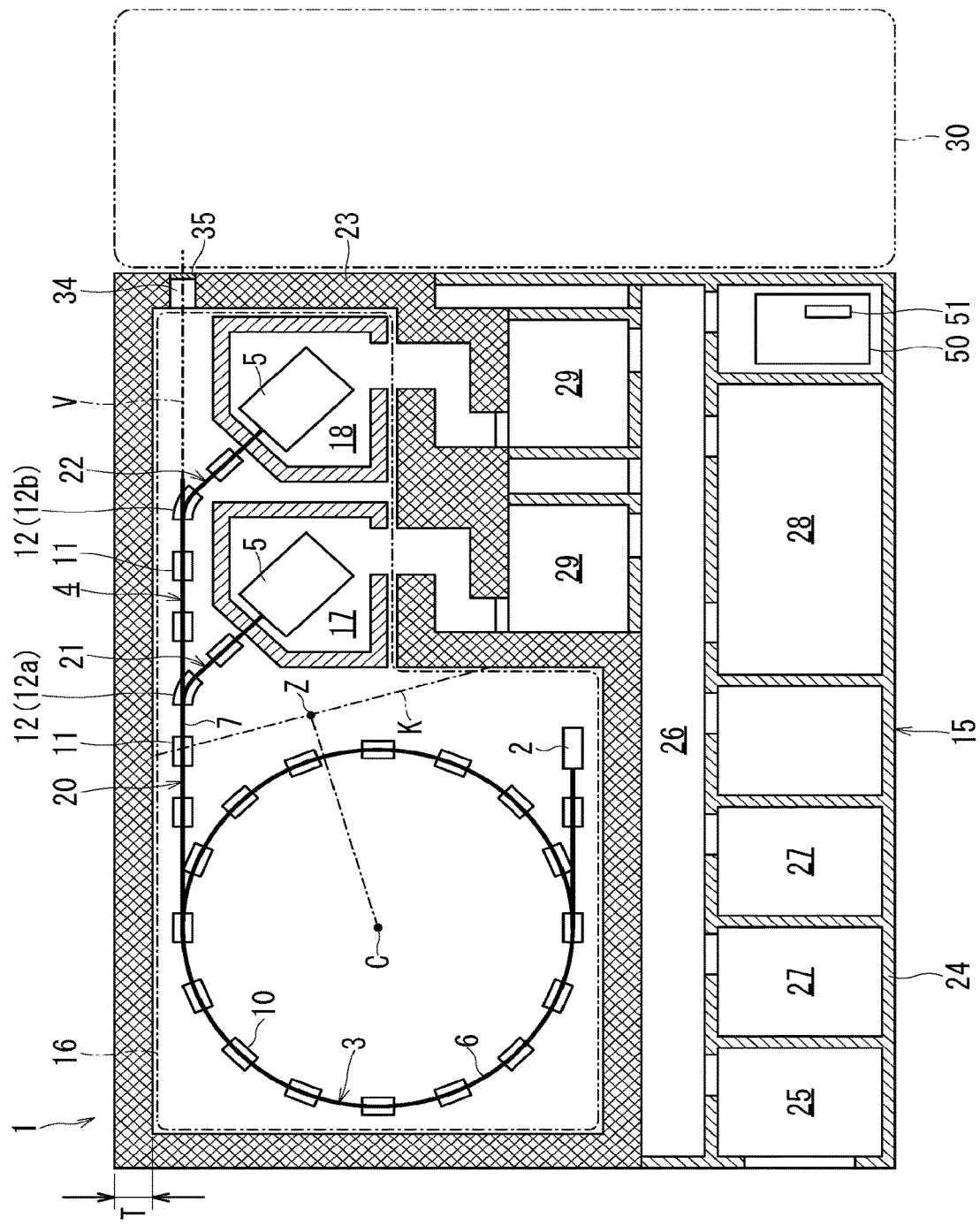
FIG. 1 is a plan view illustrating a particle beam therapy system at the time of newly constructing it in the first embodiment.

As shown in FIG. 1, the particle beam therapy system 1 includes: an ion source 2 configured to produce carbon ions that are charged particles; a ring-shaped circular accelerator 3 that accelerates carbon ions into a particle beam; a beam transportation line 4 for transporting the particle beam; and rotating gantries 5 on which a patient to be irradiated with a particle beam is placed.

First, the carbon ions generated by the ion source 2 are made incident on the circular accelerator 3. These carbon ions are accelerated to about 70% of the speed of light while orbiting the circular accelerator 3 about 1 million times, and thereby become a particle beam. This particle beam is led to two rotating gantries 5 via the beam transportation line 4.

The circular accelerator 3 includes: a high-frequency accelerating cavity that accelerates carbon ions by controlling the frequency of the magnetic field and the accelerating electric field; an injector that injects carbon ions from the ion source 2 into the circular accelerator 3; and an emission device that emits a particle beam of carbon ions from the circular accelerator 3 to the beam transportation line 4.

Figure 5:
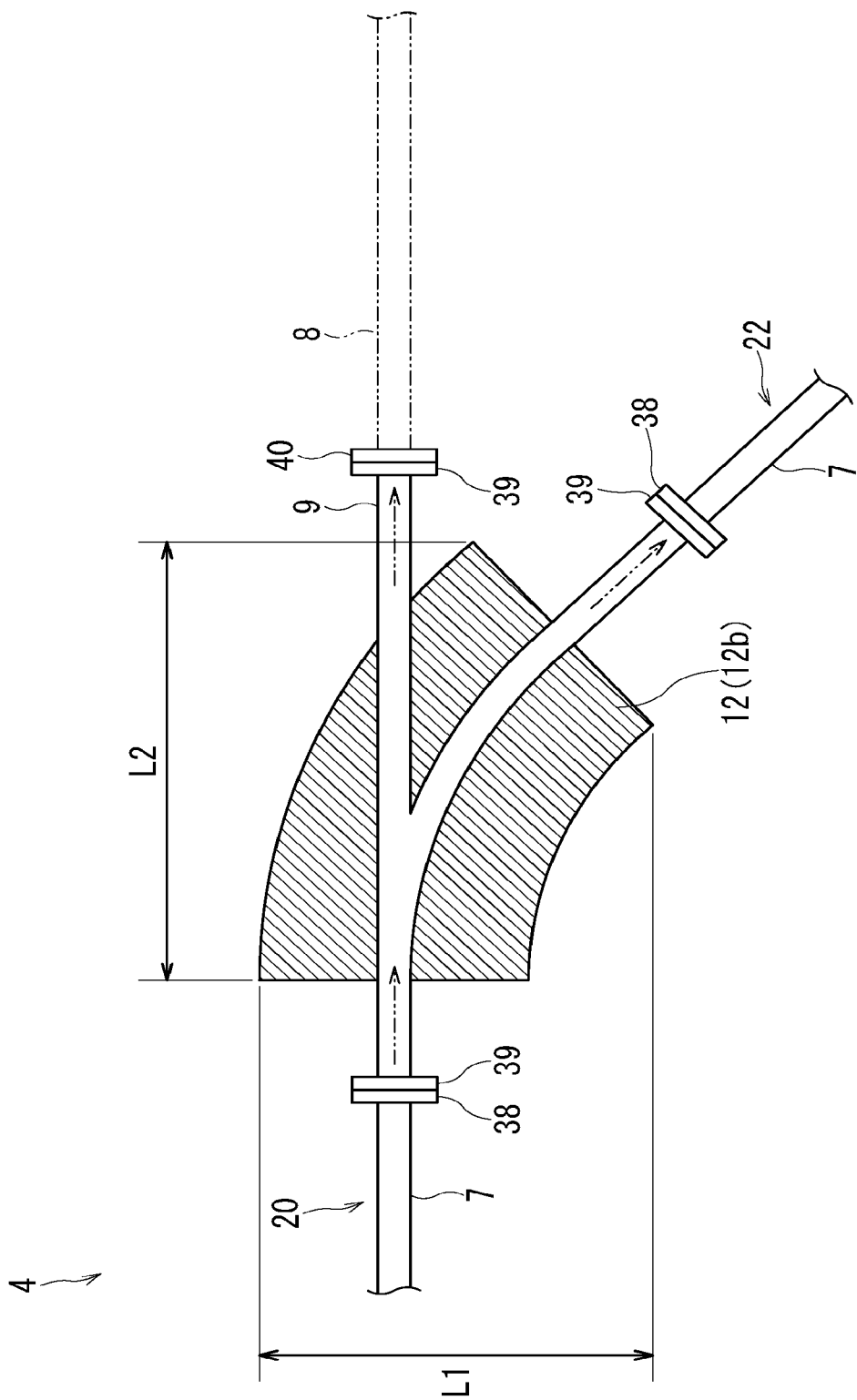
FIG. 5 is a plan view illustrating an electromagnet device.

The circular accelerator 3 and the beam transportation line 4 are provided with vacuum ducts (i.e., beam pipes) 6 to 9, inside of which are evacuated (FIG. 5). The particle beam travels inside these vacuum ducts 6 to 9. The vacuum ducts 6 to 9 of the beam transportation line 4 and the circular accelerator 3 are integrated to form a transportation route that leads the particle beam to the rotating gantries 5. That is, the vacuum ducts 6 to 9 constitute a closed continuous space that has a degree of vacuum sufficient for passing the particle beam.

Figure 2:
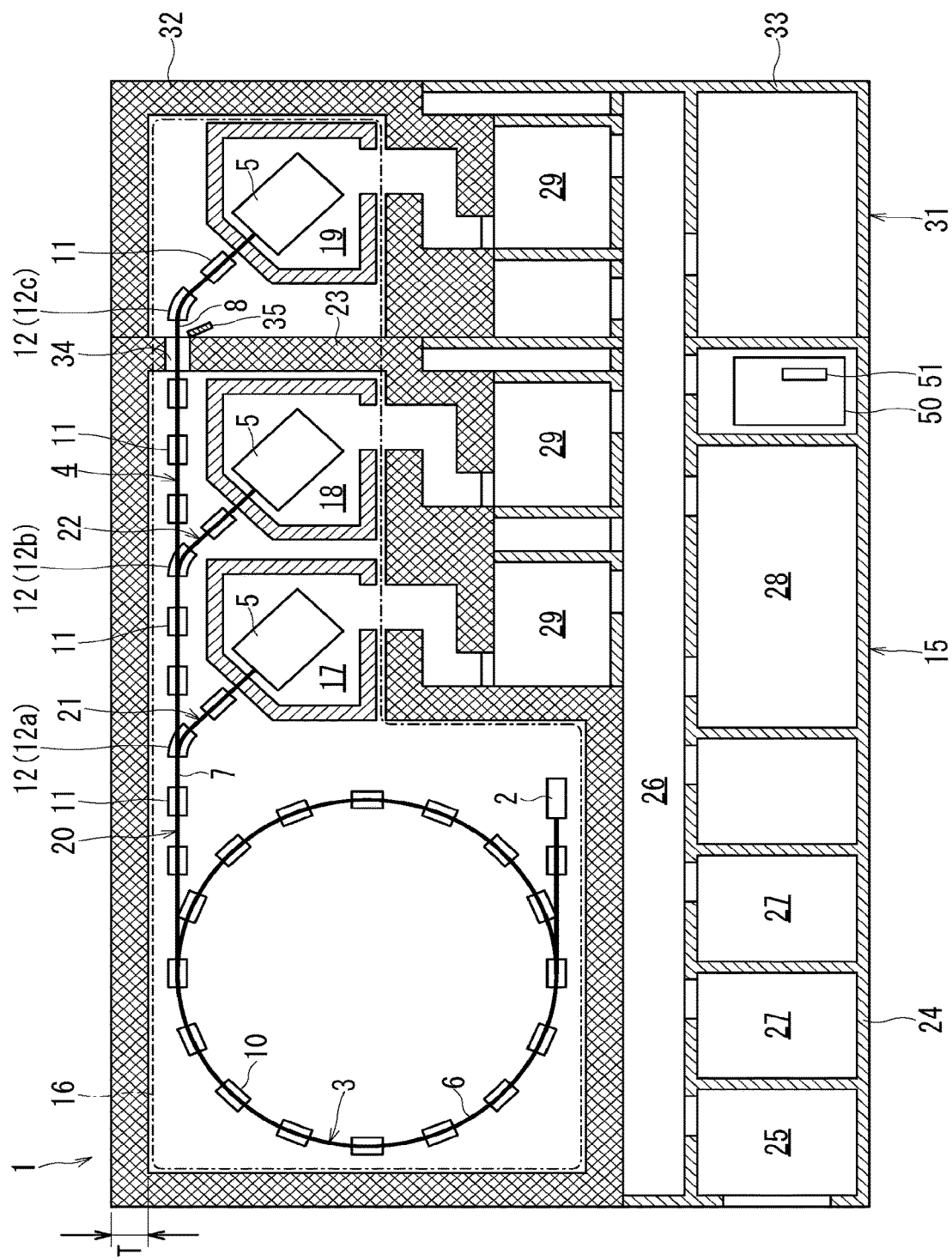
FIG. 2 is a plan view illustrating the particle beam therapy system at the time of extension in the first embodiment.

The circular accelerator 3 and beam transportation line 4 are provided with electromagnet devices 10 to 12 that control the particle beam (FIG. 2 and FIG. 5). The respective electromagnet devices 10 to 12 are disposed so as to surround the outer circumference of the vacuum ducts 6 to 9. Further, a plurality of electromagnet devices 10 to 12 are disposed along the direction in which the vacuum ducts 6 to 9 extend.

Various types of electromagnet devices 10 to 12 are used. For example, these include: a deflection electromagnet device 10 to be used in the circular accelerator 3; a quadrupole electromagnet device 11 to be used in the beam transportation line 4 for controlling the convergence and divergence of the particle beam; and a deflection electromagnet device 12 to be used for changing the traveling direction of the particle beam.

Each of the rotating gantries 5 is a large device having a cylindrical shape. Each of the rotating gantries 5 is installed such that the central axis of its cylindrical shape is along the horizontal direction. Each of the rotating gantries 5 can rotate around this axis. A vacuum duct and an electromagnet device extended from the beam transportation line 4 are attached to each of the rotating gantries 5. In each of the rotating gantries 5, the vacuum duct is first led along the central axis of the rotating gantry 5, once extends toward the cylindrical outer peripheral side of the rotating gantry 5, and then extends toward the inner peripheral side of the rotating gantry 5 again.

Each of the rotating gantries 5 are provided with an irradiator that irradiates the patient with the particle beam having been led by the beam transportation line 4. This particle beam is scanned in two directions, which are orthogonal to the beam traveling direction, so as to be radiated from the irradiator. The patient is placed on the bed inside one rotating gantry 5. This bed can be moved in the state where the patient is placed on it. This movement of the bed enables positioning by which the patient is moved to the irradiation position of the particle beam. Thus, the particle beam can be radiated onto the lesion tissue of the patient with optimum accuracy.

Further, the irradiator can be rotated around the patient by rotating the rotating gantry 5. The particle beam can be emitted from any direction around the patient. That is, each of the rotating gantries 5 is a device that can change the irradiation direction of the charged particles having been led by the beam transportation line 4 with respect to the patient. Thus, the particle beam can be accurately radiated onto the lesion portion from the optimum direction while burden on the patient is being reduced.

The particle beam loses its kinetic energy at the time of passing through the body of the patient so as to decrease its velocity and receive a resistance that is approximately inversely proportional to the square of the velocity, and stops rapidly when it decreases to a certain velocity. Near the stopping point of the particle beam, high energy called Bragg peak is emitted. The particle beam therapy system 1 matches this Bragg peak with the position of the lesion tissue (affected part) of the patient, and thus, can kill only the lesion tissue while suppressing damage to normal tissues.

As shown in FIG. 1, the particle beam therapy system 1 includes a main building 15 that houses the circular accelerator 3, the beam transportation line 4, and the rotating gantries 5. The main building 15 is a robust building made of reinforced concrete. The first embodiment illustrates the main building 15 in which the circular accelerator 3, the beam transportation line 4, and the rotating gantries 5 are all installed in the same floor.

The inside of the main building 15 is divided into a normal area and a radiation controlled area 16 including the accelerator room in which the circular accelerator 3 is installed. The radiation controlled area 16 is an area provided to prevent unnecessary entry of people and their unnecessary exposure to radiation by being clearly classified as a place where the radiation dose is a certain amount or more. The establishment of this radiation controlled area 16 is stipulated by law.

The circular accelerator 3, the beam transportation line 4, and the rotating gantries 5 are provided in the radiation controlled area 16 because they are devices that emit radioactive rays during operation. There are two rotating gantries 5 in the radiation controlled area 16 of the main building 15. The first treatment room 17 and the second treatment room 18 are provided such that the respective rotating gantries 5 are disposed in the first and second treatment rooms 17 and 18. These treatment rooms 17 and 18 are irradiation rooms in which charged particles are radiated.

The beam transportation line 4 is composed of: a main transportation line 20 extending from the circular accelerator 3; and sub-transportation lines 21 and 22 branching from the main transportation line 20 and extending to the treatment rooms 17 and 18. The deflection electromagnet device 12 capable of changing the traveling direction of the particle beam is provided in the portion where the sub-transportation lines 21 and 22 are connected to the main transportation line 20.

The main building 15 includes: a shielding wall 23 that partitions the periphery of the radiation controlled area 16 and shields radiation; and a normal wall 24 that is used in the normal area and is not supposed to shield radiation.

The shielding wall 23 prevents radiation from leaking outside the radiation controlled area 16. The thickness T of this shielding wall 23 is 1 to 2 m or more. When a metal plate such as lead or iron is provided inside the shielding wall 23, the thickness T of the shielding wall 23 may be less than 1 m. The ceiling portion of the radiation controlled area 16 is covered with a ceiling plate made of concrete and having a predetermined thickness.

Radiation is mainly generated in the beam deflecting portion and the stopping portion (i.e., disappearing portion), and is particularly generated in the tangential direction when the beam is deflected. Thus, in the case of disposing the circular accelerator 3 or the beam transportation line 4 horizontally, the structure should have sufficient shielding ability in the horizontal direction. Hence, the shielding wall 23 has a greater shielding ability than the ceiling plate.

Inside the main building 15, facilities such as a lobby 25, a corridor 26, a consultation room 27, a staff room 28, and a patient waiting room 29 are usually provided in the normal area. The human entrance path from the patient waiting room 29 to the treatment rooms 17 and 18 is formed by the shielding wall 23 and is formed into a bent crank shape in plan view. Thus, radiation does not leak from the treatment rooms 17 and 18 to the patient waiting room 29.

In the present embodiment, a controller 50 configured to control the circular accelerator 3, the beam transportation line 4, and the rotating gantries 5 is provided in the main building 15. The controller 50 includes an interlock 51 that constantly monitors whether a predetermined safety condition is satisfied or not. When the predetermined safety condition is not satisfied, the interlock 51 prohibits the operation of the circular accelerator 3. When the circular accelerator 3 is in operation and the predetermined safety condition is not satisfied, the interlock 51 causes the circular accelerator 3 to make an emergency stop.

A large budget is required to construct the particle beam therapy system 1. Thus, in the case of newly constructing the particle beam therapy system 1, the number of facilities such as treatment rooms 17 and 18 is kept low in order to reduce the initial cost. Afterward, when the management becomes stable several years after the start of operation, the number of facilities is increased by performing extension work. In the present embodiment, the extension site 30 adjacent to the main building 15 is secured in advance.

As shown in FIG. 2, the additional building 31 is provided with one rotating gantry 5. The third treatment room 19 corresponding to this rotating gantry 5 is provided. This treatment room 19 is an irradiation room where irradiation of charged particles is performed. Along with the addition of this third treatment room 19, other facilities such as the patient waiting room 29 are also added.

The additional building 31 is built so as to be integrated with the main building 15. In other words, the additional building 31 is a building that has the rotating gantry 5 to be installed in the same floor as the main building 15. The height of the floor of the additional building 31 is the same as that of the main building 15.

In this manner, at the time of newly constructing the particle beam therapy system 1, this initial cost can be reduced by reducing the installation number of rotating gantries 5 which are the most expensive devices, and after that, its operating rate can be improved by adding the rotating gantry 5.

The inside of the additional building 31 is divided into the radiation controlled area 16 and the normal area. The radiation controlled area 16 of the additional building 31 is expanded from the main building 15. Further, the additional building 31 includes: an additional shielding wall 32 that partitions the periphery of the radiation controlled area 16; and an additional normal wall 33 to be used in the normal area.

Since there is no circular accelerator 3 in the additional building 31, the beam transportation line 4 is extended from the main building 15 to the additional building 31. The beam transportation line 4 is extended through a specific portion 34 that is an additional opening portion provided in the shielding wall 23 of the main building 15. The extension is performed by connecting the beam transportation line 4 in the main building 15 and the additional beam transportation line 4 to be provided in the additional building 31. In the present embodiment, the specific portion 34 is provided in advance when the main building 15 is newly constructed.

In the following description, it is assumed that the left side of the respective sheets of FIG. 1 and FIG. 2 is the west side of the buildings 15 and 31, the right side of each sheet is the east side of the buildings 15 and 31, the upper side of the sheet is the north side of the buildings 15 and 31, and the lower side of each sheet is the south side of the buildings 15 and 31.

As shown in FIG. 1, the specific portion 34 is provided in the shielding wall 23 when the main building 15 is newly constructed. This specific portion 34 is an opening portion that penetrates the shielding wall 23. In other words, the specific portion 34 is a communication portion that communicates from the main building 15 to the additional building 31. Further, a blocking portion 35 is provided, and this blocking portion 35 closes the specific portion 34 and shields radiation passing through the specific portion 34. In the first embodiment, the blocking portion 35 is a shielding door that shields radiation.

The "outside" of the present embodiment is exemplified by the outside where no roof is provided. The specific portion 34 is provided at a position separating the outside of the shielding wall 23 from the radiation controlled area 16. For example, in main building 15 in FIG. 1, the west, north, and east walls of shielding wall 23 face the outdoors. The south wall of the shielding wall 23 faces indoors such as the patient waiting room 29. For this reason, the specific portion 34 is provided on the east side of the shielding wall 23.

Note that the "outside" in the present embodiment does not necessarily have to be outdoors and may be indoors provided with a roof as long as it is outside the radiation controlled area 16. For example, the position where the specific portion 34 is provided may be a position that separates the radiation controlled area 16 from the indoor space surrounded by the normal wall 24 that can be readily removed.

Further, the specific portion 34 is provided at a position that is on the side farther from the circular accelerator 3 in the shielding wall 23. For example, in the main building 15 in FIG. 1, the circular accelerator 3 is provided so as to be biased to the west side in the radiation controlled area 16. Thus, the specific portion 34 is provided on the east side of the wall surfaces of the shielding wall 23 facing the outdoors. When a boundary K is defined as a line that passes through the centroid Z of the radiation controlled area 16 and is orthogonal to the line connecting the centroid Z and the center C of the circular accelerator 3, the above-described disposition is the position of the region (i.e., east-side region) opposite to the west-side region where the center C of the circular accelerator 3 is located with respect to this boundary K. That is, the specific portion 34 is provided at the position opposite to the region where the center C of the circular accelerator 3 is located with respect to the centroid Z of the radiation controlled area 16 in plan view.

The "centroid" in the present embodiment is the position of the center of gravity of the figure, and is the point at which the figure balances in the case of using the position as the fulcrum. For example, when the figure is a rectangle, its centroid is the intersection of the diagonals of the rectangle.

The circular accelerator 3 and the treatment rooms 17 and 18 are provided in the radiation controlled area 16. When the circular accelerator 3 is installed in one side in the radiation controlled area 16, the treatment rooms 17 and 18 are installed in the other side. In this manner, in the case of adding the treatment room 19 close to the treatment rooms 17 and 18, the beam transportation line 4 can be extended in a short distance from the main building 15 to the additional building 31 through the specific portion 34.

The specific portion 34 is provided further ahead in the direction in which the main transportation line 20 extends. In the main building 15 in FIG. 1, the main transportation line 20 extends from the circular accelerator 3 on the west side to the east side, and the particle beam is transported from the west side to the east side. For this reason, the specific portion 34 is provided at a position where the shielding wall 23 intersects with the virtual line V obtained by extending the main transportation line 20 downstream in the transportation direction. In this manner, when the third treatment room 19 is added, the beam transportation line 4 can be extended to the additional building 31 without providing an additional deflection electromagnet device 12 in the main building 15.

At the end of the main transportation line 20, a sub-transportation line 22 extending to the second treatment room 18 located farthest from the circular accelerator 3 is provided. A deflection electromagnet device 12b is provided at the connection portion between this sub-transportation line 22 and the main transportation line 20. The specific portion 34 may be provided near this deflection electromagnet device 12b.

The specific portion 34 is disposed at a position that separates the radiation controlled area 16 from the extension site 30 of the third treatment room 19 in the shielding wall 23. In the main building 15 in FIG. 1, the extension site 30 is provided on the east side of the main building 15. Accordingly, the specific portion 34 is provided on the east side of the shielding wall 23. In this manner, an additional opening portion can be provided near the extension site 30 of the third treatment room 19, and thus, the extension path of the beam transportation line 4 can be minimized.

Figure 3:
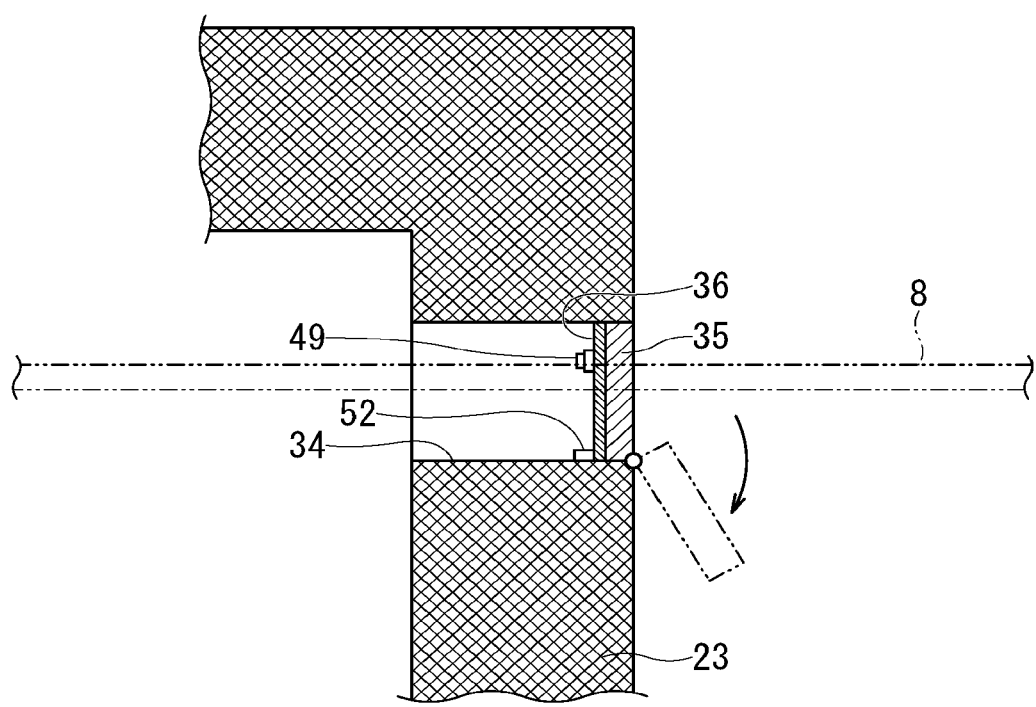
FIG. 3 is a plan view illustrating a specific portion and a blocking portion in the first embodiment.
Figure 4:
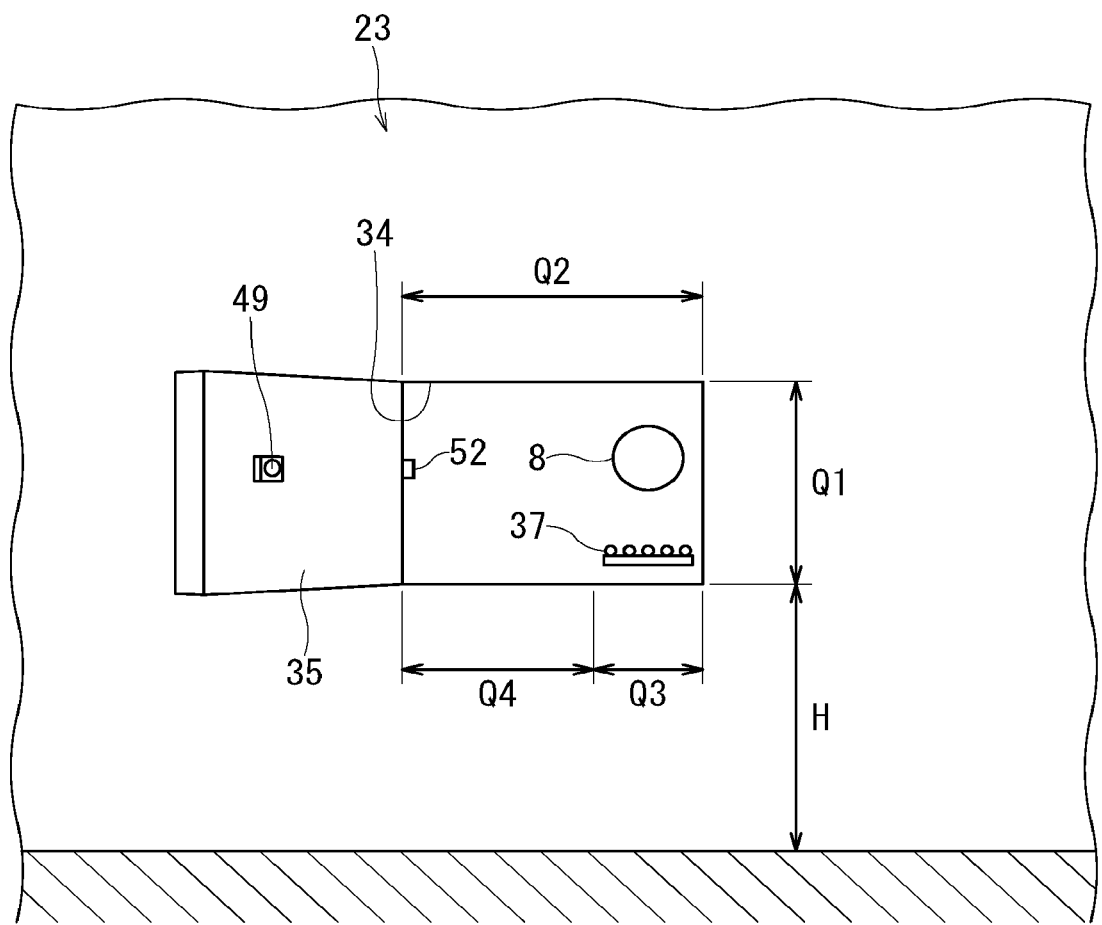
FIG. 4 is a side view illustrating the specific portion and the blocking portion in the first embodiment.

As shown in FIG. 3 and FIG. 4, the specific portion 34 is an opening portion having a rectangular shape in side view. This specific portion 34 is formed by horizontally penetrating the shielding wall 23 when the main building 15 is newly constructed. The blocking portion 35 for closing the specific portion 34 is a shielding door that is provided with a metal plate 36 such as lead or iron inside. Since the specific portion 34 is closed with the blocking portion 35, radiation does not leak to the outside from the radiation controlled area 16.

The opening dimension Q1 of the specific portion 34 in the vertical direction is approximately 60 cm. The opening dimension Q1 of the specific portion 34 in the lateral direction is approximately 80 cm. The vertical and lateral opening dimensions Q1 and Q2 of the specific portion 34 are preferably 1 m or less. For example, the dimension L1 in the lateral direction and the dimension L2 in the longitudinal direction of the deflection electromagnet device 12 to be used in the beam transportation line 4 are about 1 to 2 m (FIG. 5). The opening dimensions Q1 and Q2 of the specific portion 34 are set in such a manner that the deflection electromagnet device 12 cannot pass through the specific portion 34. The dimension of other electromagnet devices is also about 1 to 2 m.

Since the vertical and lateral opening dimensions Q1 and Q2 of the specific portion 34 are 1 m or less, cables 37 and a vacuum duct 8 constituting an additional beam transportation line 4 can be installed via the specific portion 34 with its opening dimension minimized. Since the opening dimension is minimized, the robustness of the main building 15 can be maintained and the thickness of the shielding wall 23 can be minimized.

Under the state where the specific portion 34 is opened, various cables 37 and the vacuum duct 8 of the additional beam transportation line 4 are installed across the main building 15 and the additional building 31. Of the opening dimension Q2 of the specific portion 34 in the lateral direction, the opening dimension Q3 on the right side is used to lead out the vacuum duct 8 and the various cables 37. This opening dimension Q3 is about 20 cm. This opening dimension Q3 is a dimension corresponding to the diameter of the vacuum duct 8.

The opening dimension Q4 on the left side is used by an operator who performs the extension work to move back and forth between the main building 15 and the additional building 31. This opening dimension Q4 is about 60 cm. Further, the specific portion 34 is provided at a predetermined height position H from the floor surface. This height position H is about 1 m. This height position H is set depending on the height position of the existing vacuum duct 7.

In the specific portion 34 of the present embodiment, it is preferred to secure another opening portion that is different from both of the entrance/exit to be used by people as a normal approach path and a carry-in entrance of equipment at the time of newly constructing the building. In other words, in the shielding wall 23 of the main building 15, the specific portion 34 is provided in addition to the normal entrance/exit of people and the carry-in entrance of equipment at the time of newly constructing the building.

The carry-in entrance of equipment such as electromagnet devices 10 to 12 at the time of newly constructing the building is provided in the ceiling portion of the radiation controlled area 16. This carry-in entrance is covered with a ceiling plate made of concrete after carrying in the equipment.

The carry-in entrance of equipment at the time of newly constructing the building may be provided on the shielding wall 23. In this case, however, the opening dimension of the carry-in entrance will be about 5 m at maximum, so the structure of the building will be fragile as it is, and consequently, the thickness of the shielding wall 23 needs to be thicker than required for the shielding performance. For this reason, after the equipment has been carried in, it will be reconstructed and the carry-in entrance will be blocked with the same structure as the surrounding area. At this time, the specific portion 34 can be provided by adjusting the opening dimension without completely closing the opening. Incidentally, the carry-in entrance may be provided at an appropriate position for providing the specific portion 34 and this carry-in entrance may be used as the specific portion 34.

At the time of loading the equipment at the new construction there is no need for radiation control because it is before the start of operation. Thus, in the conventional carry-in entrance of equipment at the time of newly constructing the building, sufficient measures are not taken against radiation leakage. Contrastively, the shielding door that is the blocking portion 35 in the first embodiment is a door that does not open during normal times after starting treatment. Thus, no handle is provided on this shielding door. Further, this shielding door is provided with an operation unit 49 that can be opened only from the side of the radiation controlled area 16 in the shielding wall 23. This operation unit 49 is a lock that can be unlocked only from the side of the radiation controlled area 16. In other words, the shielding door is a mechanism that can be opened only from the inside (i.e., radiation controlled area 16). At the time of operating the operation unit 49 in order to open the shielding door, a predetermined tool (for example, a detachable handle) is used to open it. A handle may be provided on the shielding door in the same manner as a normal door.

Until the extension work is completed, the interlock 51 (FIG. 1) stops the operation of the device when the blocking state of the blocking portion 35 changes due to opening of the shielding door. This can prevent unintended leakage of radiation after the start of treatment.

As shown in FIG. 3 and FIG. 4, an opening/closing sensor 52 configured to detect an open/closed state is provided in the blocking portion 35 that is a shielding door. On the basis of the information acquired by the opening/closing sensor 52, the interlock 51 (FIG. 1) of the controller 50 determines whether the shielding door is opened or not. When the shielding door is opened and the circular accelerator 3 is in operation, processing of urgently stopping the operation of the circular accelerator 3 is performed.

In the present embodiment, at the time of newly constructing the main building 15, the specific portion 34 is constructed in advance. Afterward, at the time of constructing the additional building 31, an additional opening portion can be readily provided on the shielding wall 23 by opening the specific portion 34. Since destruction of the shielding wall 23 is not necessary for forming the additional opening portion, the construction period can be significantly shortened. The work of removing the blocking portion 35 is usually completed within 1 day, in about 2 hours.

When the extension work (i.e., construction of the additional building 31) is performed, the shielding wall 32 of the additional building 31 is constructed in advance. Further, equipment such as the additional vacuum duct 8, the quadrupole electromagnet device 11, the deflection electromagnet device 12c, and the rotating gantry 5 is carried into the additional building 31 and assembled. These works can be performed during the day while usual treatment is being continued in the main building 15. After the equipment of the additional building 31 is installed, the specific portion 34 is opened, and the vacuum duct 7 of the beam transportation line 4 of the main building 15 is connected to the vacuum duct 8 of the beam transportation line 4 of the additional building 31. In other words, the connection work between the existing vacuum duct 7 and the additional vacuum duct 8 is performed at the end of the equipment assembly process.

The work of opening the specific portion 34 and connecting the vacuum ducts 7 and 8 can be done in about one day. In other words, when this work is performed in a period during which normal treatment is not performed in the main building 15 (for example, at night or on holidays such as weekends), the extension work can be completed without reducing the operating rate of the particle beam therapy system 1.

As in the conventional technology, in the case of providing an opening for the shielding wall 23 that separates the radiation controlled area 16 from the outside, the equipment such as the circular accelerator 3 must be stopped in order to prevent radiation from leaking to the outside. This is because the construction will not be completed in one day and appropriate radiation shielding will be required during or after the opening is provided. Even if the problem of radiation is solved, vibration (noise) generated at the time of making a hole in the wall adversely affects the treatment, and thus, the construction must be interrupted during the treatment. In the conventional technology, there is a period during which normal medical treatment cannot be performed, because the equipment has to be stopped at the time of constructing the additional opening portion in the shielding wall 23.

However, in the present embodiment, the specific portion 34 is provided in advance of newly constructing the main building 15, and thus, the period during which normal treatment cannot be performed can be eliminated at the time of the extension work. Further, there is no need to perform large-scale construction in the main building 15 at the time of the extension work.

In particular, in particle beam therapy, it is generally necessary to continue treatment for 3 to 4 days per week for several weeks. Thus, if there is a period during which treatment cannot be performed for 4 days or more, the treatment will have to be restarted from the beginning. In the present embodiment, it is not necessary to interrupt the treatment even in the case of adding equipment. Thus, the operation rate of the particle beam therapy system 1 can be improved.

When the additional building 31 is constructed, it is necessary to perform positioning on both of the existing equipment and the additional equipment before both are actually connected. When the blocking portion 35 is opened in such a case, the positioning of the additional equipment can be performed in accordance with the existing equipment, and after the positioning is completed, the opening can be closed immediately to block radiation. In the positioning, in addition to the equipment installation work, the reference point may be transferred. This work can also be performed in a period during which normal treatment is not performed such as nighttime or holidays including weekends. Since the blocking portion 35 can be opened and closed as necessary, the treatment using the particle beam therapy system 1 can be continued even in the period of the extension work.

As shown in FIG. 5, the beam transportation line 4 includes: normal vacuum ducts 7 and 8 having no branch; and a branching vacuum duct 9 to be branched in two directions. The branching vacuum duct 9 is provided at the branch portion of the main transportation line 20 and the sub-transportation lines 21 and 22 (FIG. 1). A flange 38 for connection is provided at the ends of the normal vacuum ducts 7 and 8, and another flange 39 for connection is also provided at the end of the branching vacuum duct 9.

At these branch portions, deflection electromagnet devices 12a and 12b are provided (FIG. 1). The magnetic field to be generated by these deflection electromagnet devices 12a and 12b enables the particle beam traveling along the main transportation line 20 to move straight or bend toward the sub-transportation lines 21 and 22.

At the time of newly constructing the main building 15, the sub-transportation line 22 extending to the second treatment room 18 is connected to the end of the main transportation line 20, but it does not need to be branched. However, the sub-transportation line 22 is connected to the main transportation line 20 by using the branching vacuum duct 9 in advance.

A closing flange 40 is attached to the flange 39 at one end of the branching vacuum duct 9. The closing flange 40 closes one end of the branching vacuum duct 9. One end of the branching vacuum duct 9 serves as a connecting portion to which the additional vacuum duct 8 can be connected. Further, this branching vacuum duct 9 is provided in the portion closest to the specific portion 34 in the beam transportation line 4 of the main building 15.

A closing valve may be provided on the flange 39 at one end of the branching vacuum duct 9. In this manner, when the additional vacuum duct 8 is connected to one end of the branching vacuum duct 9 via a closing valve and opening and closing of this closing valve is appropriately performed, the beam transportation line 4 can be tested or adjusted.

At the time of constructing the additional building 31, the closing flange 40 is removed from the branching vacuum duct 9, and thereby, the additional vacuum duct 8 can be connected. In this manner, at the time of constructing the additional building 31, the additional vacuum duct 8 can be connected without replacing the parts of the beam transportation line 4 of the main building 15, and thus, the work can be completed in a short period.

Although the branching vacuum duct 9 is provided at the end of the main transportation line 20 at the time of newly constructing the main building 15 in the present embodiment, another aspect may be adopted.

For example, at the time of newly constructing the main building 15, the sub-transportation line 22 is connected to the end of the main transportation line 20 via a vacuum duct bent in one direction. In this aspect, during the regular inspection period of the particle beam therapy system 1, the vacuum duct bent in one direction at the end of the main transportation line 20 may be replaced by the branching vacuum duct 9.

In the present embodiment, the controller 50 configured to control the circular accelerator 3, the beam transportation line 4, and the rotating gantries 5 is provided in the main building 15. When another beam transportation line 4 and another rotating gantry 5 are added, the controller for controlling these added devices may be added to the additional building 31 or the existing controller 50 in the main building 15 may be used for controlling these added devices.

Figure 6:
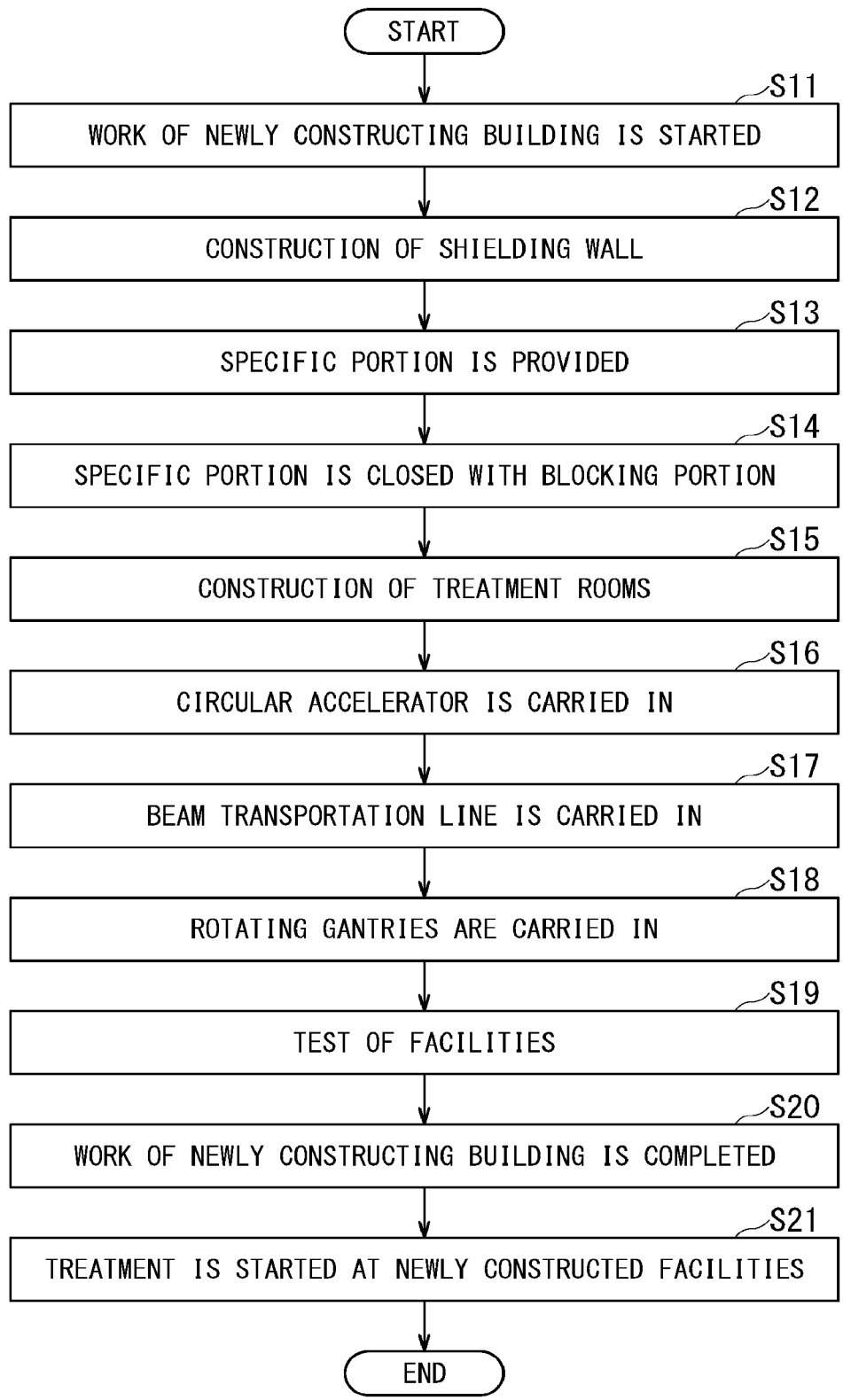
FIG. 6 is a flowchart illustrating a particle beam therapy system construction method at the time of newly constructing it.

Next, a particle beam therapy system construction method at time of newly constructing it will be described by referring to the flowchart of FIG. 6.

First, in the next step S11, work of newly constructing the main building 15 is started.

In the next step S12, the shielding wall 23 of the main building 15 is constructed.

In the next step S13, the specific portion 34 is provided on the shielding wall 23 of the main building 15.

In the next step S14, the specific portion 34 is closed with the blocking portion 35.

In the next step S15, the treatment rooms 17 and 18 of the main building 15 are constructed.

In the next step S16, the circular accelerator 3 is carried into the radiation controlled area 16 of the main building 15.

In the next step S17, the beam transportation line 4 is carried into the radiation controlled area 16 of the main building 15.

In the next step S18, the rotating gantries 5 are carried into the respective treatment rooms 17 and 18 of the main building 15.

In the next step S19, test or adjustment is performed on various facilities having been carried into the main building 15, such as the circular accelerator 3, the beam transportation line 4, and the rotating gantries.

In the next step S20, the work of newly constructing the main building 15 is completed.

In the next step S21, treatment is started at the new facilities in the main building 15.

Figure 7:
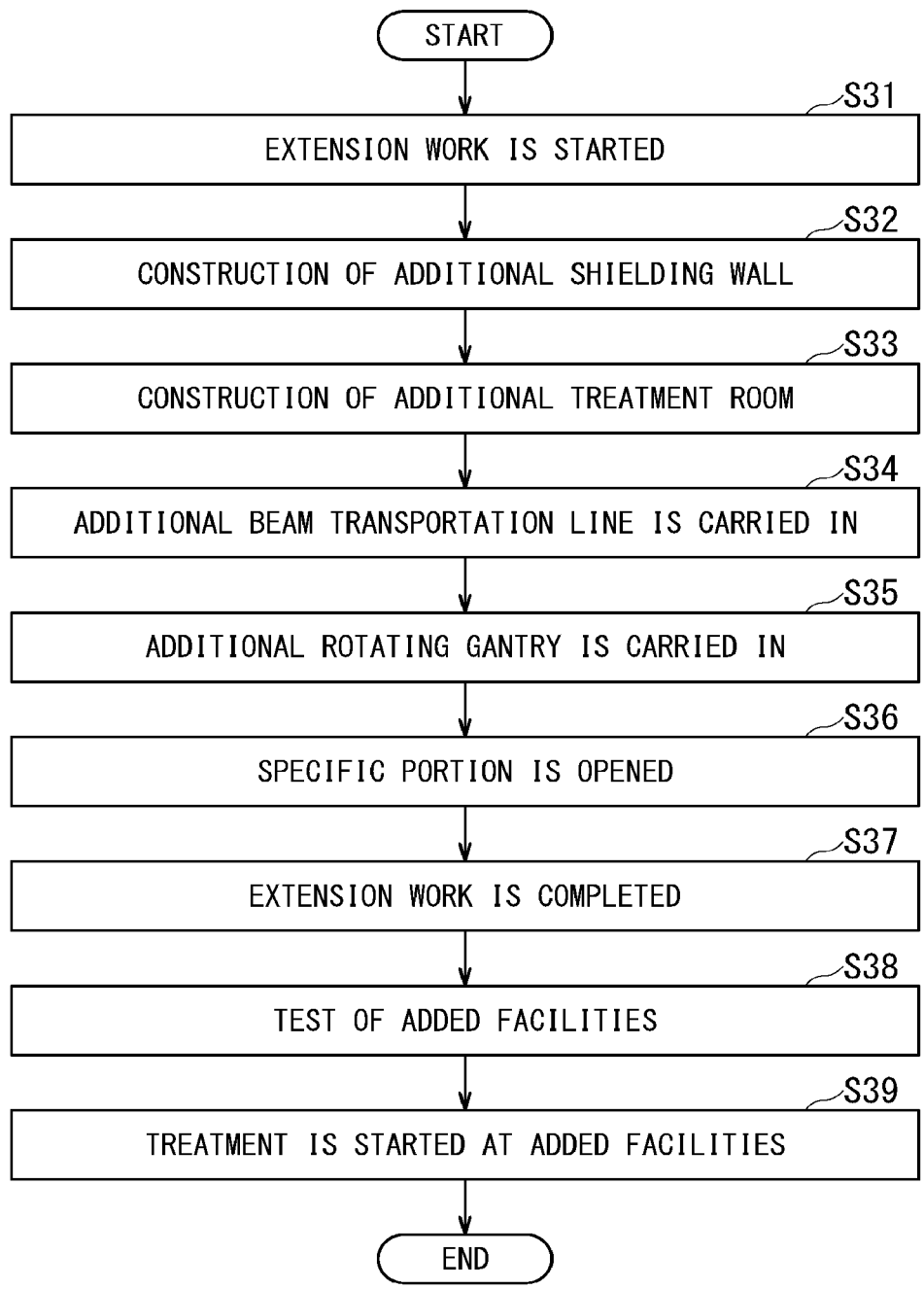
FIG. 7 is a flowchart illustrating a particle beam therapy system construction method at the time of extension.

Next, a particle beam therapy system construction method at time of extension work (i.e., additionally constructing a building) will be described by referring to the flowchart of FIG. 7.

First, in the next step S31, extension work is started at the extension site 30 adjacent to the main building 15. The treatment using the equipment of the main building 15 is continued.

In the next step S32, the additional shielding wall 32 of the additional building 31 is constructed.

In the next step S33, the third treatment room 19 of the additional building 31 is constructed.

In the next step S34, another beam transportation line 4 is carried into the additional building 31.

In the next step S35, another rotating gantry 5 is carried into the third treatment room 19 of the additional building 31.

In the next step S36, the blocking portion 35 closing the specific portion 34 of the main building 15 is operated such that the specific portion 34 is opened. The beam transportation line 4 of the main building 15 and the beam transportation line 4 of additional building 31 are connected. These works can be performed on holidays or at night. At this time, the additional shielding wall 32 is already constructed, and thus, it is easy to set the radiation controlled area 16 and there is no need to worry about shielding after opening the specific portion 34.

In the next step S37, the extension work of the additional building 31 is completed.

In the next step S38, on other holidays or during another night period, test or adjustment is performed on various facilities having been carried into additional building 31, such as the circular accelerator 3, the beam transportation line 4, and the rotating gantry 5.

In the next step S39, treatment is started using the added facilities in the additional building 31.

(Second Embodiment)

Next, the specific portion 34A and the blocking portion 35A of the second embodiment will be described by referring to FIG. 8. The same components as those shown in the above-described embodiment are denoted by the same reference signs, and duplicate description is omitted.

Figure 8:
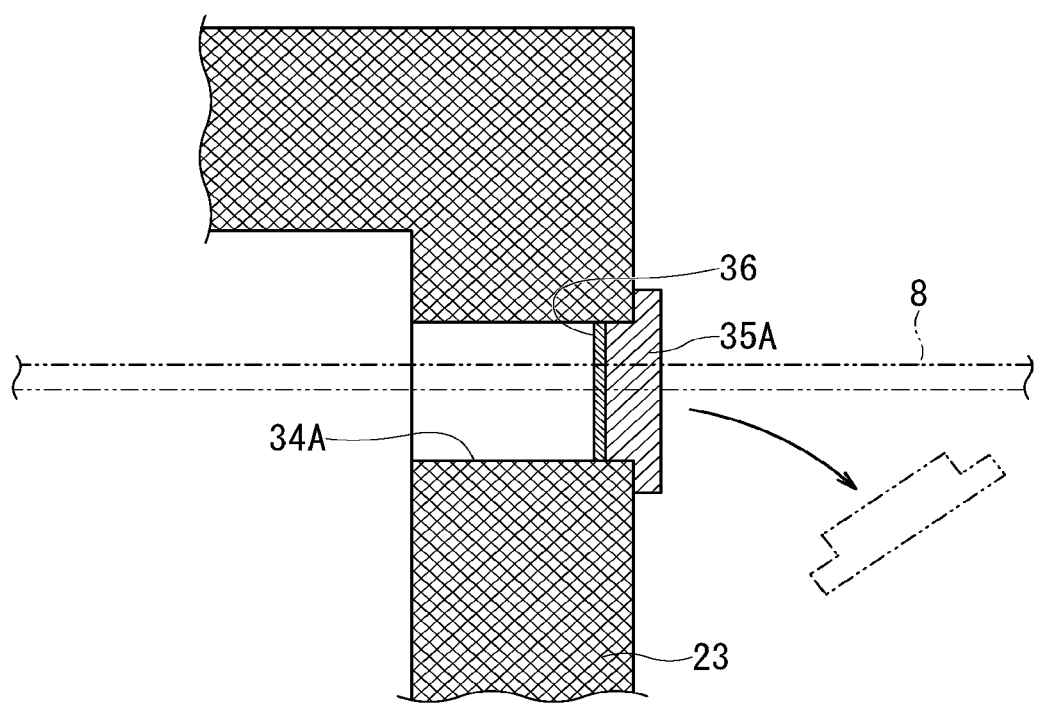
FIG. 8 is a plan view illustrating the specific portion and the blocking portion in the second embodiment.

As shown in FIG. 8, the specific portion 34A of the second embodiment is formed by horizontally penetrating the shielding wall 23 when the main building 15 is newly constructed. This specific portion 34A is provided on the shielding wall 23 at the time of newly constructing the main building 15, similarly to the first embodiment. Further, the position where the specific portion 34A is provided is also the position that separates the outside of the shielding wall 23 from the radiation controlled area 16, similarly to the first embodiment.

The blocking portion 35A for closing the specific portion 34A is a shielding block in which a metal plate 36 such as lead or iron is provided. The blocking portion 35A is a member having a convex shape in cross-section. The member may not be integrated but may be divided into a plurality of parts for easy handling. This blocking portion 35A can be attached to the specific portion 34A from the outside. Further, the blocking portion 35A can be removed from the specific portion 34A.

The blocking portion 35A may be locked such that it cannot be readily opened. Further, the blocking portion 35A may be provided with the operation unit 49 that can be released only from the side of the radiation controlled area 16. That is, the blocking portion 35A may be a mechanism that can be opened only from the inside (i.e., from the radiation controlled area 16). Further, the interlock 51 may be provided to stop the operation of the device when the closing state of the blocking portion 35A changes.

When the additional building 31 is constructed, under the state where the specific portion 34A is opened, various cables 37 and the additional vacuum duct 8 of the beam transportation line 4 are led from the main building 15 to the additional building 31. Radiation does not leak from the radiation controlled area 16 to the outside by closing the specific portion 34A with this blocking portion 35A.

When the main building 15 is newly constructed, the blocking portion 35A configured as a heavy and strong shielding block is attached to the specific portion 34A. In this case, when the additional building 31 is constructed, this heavy and strong blocking portion 35A may be replaced by another blocking portion 35A that is a lightweight and simple shielding block. Since it is replaced by a lightweight shielding block, it becomes easier to attach and detach the blocking portion 35A at the time of constructing the additional building 31.

In the second embodiment, the blocking portion 35A is a shielding block that can be attached to and detached from the specific portion 34A. Thus, when an additional treatment room is constructed, the work of opening the additional opening portion can be readily performed without breaking the shielding wall 23.

(Third Embodiment)

Next, the specific portion 34B and the blocking portion 35B of the third embodiment will be described by referring to FIG. 9 and FIG. 10. The same components as those shown in the above-described embodiments are denoted by the same reference signs, and duplicate description is omitted.

Figure 9:
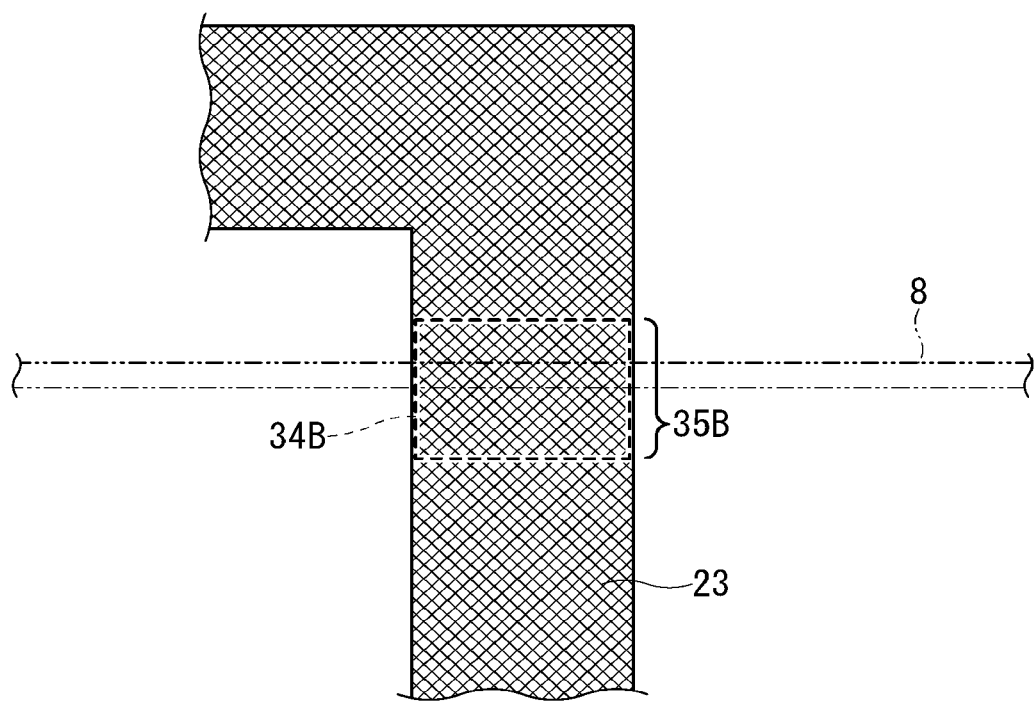
FIG. 9 is a plan view illustrating the specific portion and the blocking portion in the third embodiment.

As shown in FIG. 9, the specific portion 34B of the third embodiment is provided in the shielding wall 23 when the main building 15 is newly constructed, similarly to the first embodiment. Further, the position where the specific portion 34B is provided is also the position that separates the outside of the shielding wall 23 from the radiation controlled area 16, similarly to the first embodiment. When the main building 15 is newly constructed, the specific portion 34B is closed with the blocking portion 35B that constitutes part of the shielding wall 23.

Figure 10:
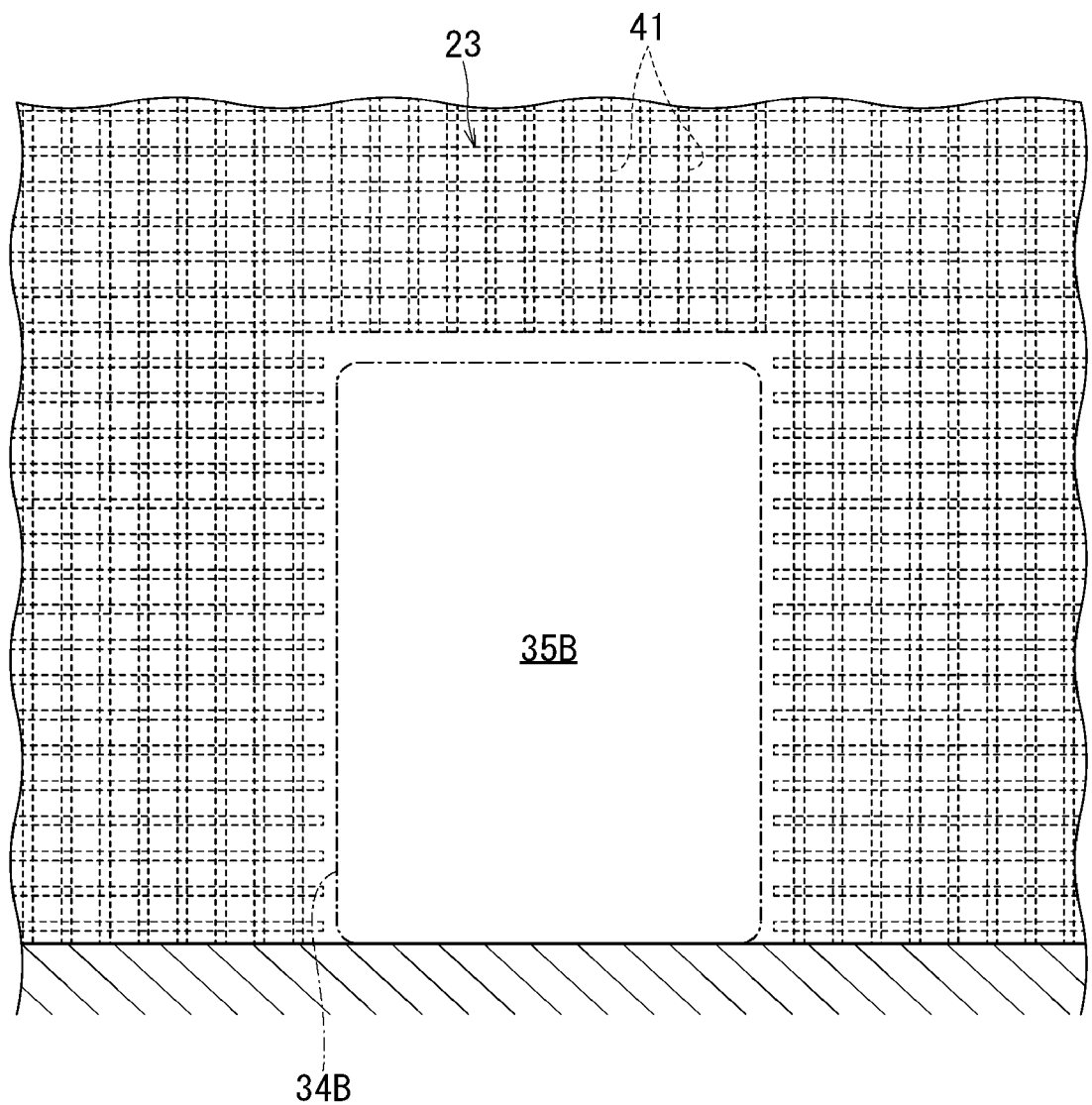
FIG. 10 is a side view illustrating the specific portion and the blocking portion in the third embodiment.

As shown in FIG. 10, most of the shielding wall 23 is formed of reinforced concrete having reinforcing steel rods 41 inside. The blocking portion 35B for closing the specific portion 34B is made of unreinforced concrete without the reinforcing steel rods 41 inside. That is, the blocking portion 35B is a portion formed to have weaker strength than other portions of the shielding wall 23. In this manner, while the radiation is being shielded by concrete, the portion formed of unreinforced concrete can be configured as the blocking portion 35B that is lower in strength than other portions of the shielding wall 23.

When the additional building 31 is constructed, work of penetrating the blocking portion 35B made of unreinforced concrete is performed, and thereby, an additional opening portion is formed in the specific portion 34B. This specific portion 34B has a dimension such that it is opened from the floor surface to a predetermined height position.

In the third embodiment, the blocking portion 35B is a portion that forms part of the shielding wall 23 and is weaker in strength than other portions of the shielding wall 23. Thus, while a large opening portion is being secured, the work of forming the additional opening portion can be performed in a short period when an additional treatment room is constructed.

(Fourth Embodiment)

Next, the specific portion 34C and the blocking portion 35C of the fourth embodiment will be described by referring to FIG. 11. The same components as those shown in the above-described embodiments are denoted by the same reference signs, and duplicate description is omitted.

Figure 11:
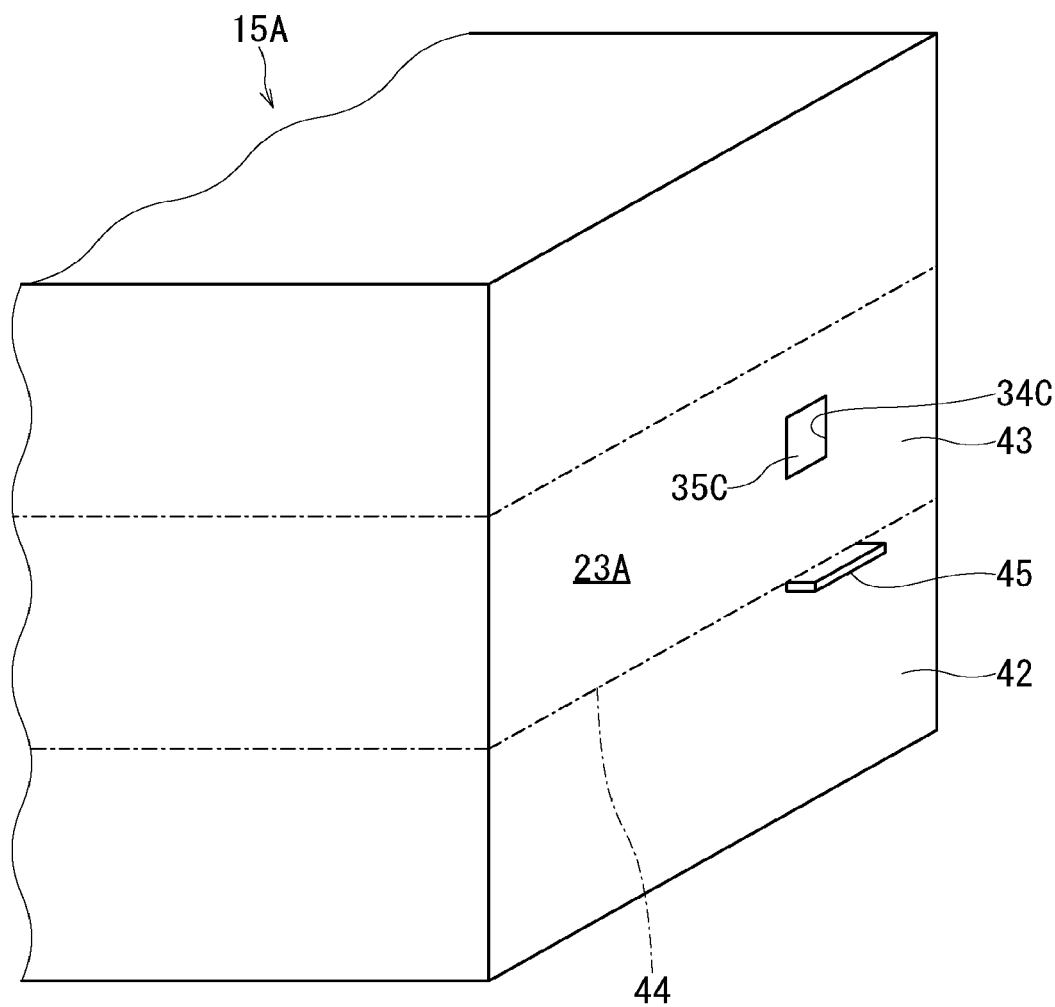
FIG. 11 is a perspective view illustrating the specific portion and a floor reference portion in the fourth embodiment.

As shown in FIG. 11, in the fourth embodiment, a main building 15A in which a circular accelerator 3 and rotating gantries 5 are installed in different floors is illustrated. Adjacent to this main building 15A, an additional building with the same number of floors is constructed. In the case of the main building 15A with two or more floors, the circular accelerator 3 may be installed on the first floor 42 and the specific portion 34C may be provided on the second floor 43 or on a higher floor. In this main building 15A, the specific portion 34C is provided in the shielding wall 23A on the second floor 43. This specific portion 34C is closed with a lid-shaped blocking portion 35C.

Even when the floor where the circular accelerator 3 is provided is different from the floor where the specific portion 34C is provided, the specific portion 34C is provided at the position that separates the outside of the shielding wall 23A from the radiation controlled area 16 in plan view. The specific portion 34C is provided at the position where the shielding wall 23A intersects with the virtual line obtained by extending the main transportation line 20 in the transportation direction in plan view, i.e., provided at the position further ahead in the direction in which the main transportation line 20 extends in plan view. In plan view, the specific portion 34C is provided at the position on the farther side from the circular accelerator 3 in the shielding wall 23A.

The configuration of the fourth embodiment is provided with a floor reference portion 45 configured to indicate the height position of the floor surface 44 of the second floor 43 where the specific portion 34C exists. The floor reference portion 45 is provided at the position corresponding to the lower position of the specific portion 34C. The floor reference portion 45 is a plate-shaped portion that protrudes laterally from the outdoor wall surface of the shielding wall 23A on the second floor 43. The top face of the floor reference portion 45 coincides with the height position of the floor surface 44 of the second floor 43.

In this manner, at the time of constructing the additional building, the workers can check the height position of the floor surface 44 of the main building 15A (i.e., height serving as the reference for installing the equipment) by the floor reference portion 45 from the outdoor side of the shielding wall 23A without entering the radiation controlled area 16. On the basis of the checked height position of the floor surface 44 of the main building 15A, the height position of the floor surface of the second floor of the additional building can be determined. In other words, though highly accurate installation position of 1 mm or less is required, height deviation between the existing equipment and the additional equipment is prevented, and thereby, returning of the process at the time of connecting the beam transportation line 4 can be prevented.

The floor reference portion 45 is provided on the second floor 43 of the main building 15A in the fourth embodiment. However, when the floor corresponding to the specific portion 34C is the first floor or the basement floor, the floor reference portion 45 may be provided on the wall surface on the outdoor side of the shielding wall on the first floor or the basement floor.

Although the floor reference portion 45 is a plate-shaped portion that protrudes laterally from the wall surface, this floor reference portion 45 may be a recess formed by denting the wall surface. Further, the floor reference portion 45 may be a marker provided on the wall surface.

Although the particle beam therapy system has been described on the basis of the first to fourth embodiments, the configuration applied in any one of the embodiments may be applied to other embodiments or the configurations in the respective embodiments may be applied in combination. For example, the opening dimension of the additional opening portion of the first embodiment may be the dimension of the additional opening portion of another embodiment.

Although a mode in which each step is executed in series is illustrated in the flowcharts of in the above-described embodiments, the execution order of the respective steps is not necessarily fixed and the execution order of part of the steps may be changed. Additionally, some steps may be executed in parallel with another step.

Although the rotating gantry 5 is provided in the treatment room 19 as an additional irradiation room in the above-described embodiments, another aspect may be adopted. For example, the treatment room may be a fixed room in which an irradiator for irradiating a patient with the particle beam is fixedly disposed without providing the rotating gantry 5. Further, the irradiation room as a target of the extension work may not be the treatment room 19 but may be an experiment room or the beam checking room.

Although the floor height of the additional building 31 is the same as the floor height of the main building 15 in the above-described embodiments, the additional building 31 and the main building 15 may be on the same floor or the floor heights of both may be slightly different. A two-story additional building 31 may be constructed adjacent to the one-story main building 15 and these buildings 15 and 31 may be connected to each other.

Although the additional building 31 is constructed so as to be integrated with the main building 15 in the above-described embodiments, the additional building 31 may be constructed at a position away from the main building 15. In this case, a connection passage extending from the specific portion 34 to the additional building 31 may be formed, and the beam transportation line may be extended by this passage from the main building 15 to the additional building 31.

Although the specific portion 34 penetrates the shielding wall 23 in the horizontal direction in the above-described embodiments, another aspect may be adopted. For example, when the beam transportation line 4 is disposed diagonally with respect to the horizontal plane, the specific portion 34 may penetrate the shielding wall 23 in a slanting direction. Further, the specific portion 34 may be bent inside the shielding wall 23.

Although the specific portion 34 is provided on the shielding wall 23 in the above-described embodiments, the specific portion 34 may be provided on the ceiling (i.e., shielding wall) that partitions the radiation controlled area 16. That is, the specific portion 34 may vertically penetrate the ceiling.

Although the specific portion 34 is provided on the shielding wall 23 on the ground floor in the above-described embodiments, the specific portion 34 may be provided on the shielding wall 23 on the basement floor.

Although the facilities for performing heavy-ion-beam cancer treatment are illustrated in the above-described embodiments, the above-described embodiments can be applied to other facilities. For example, the above-described embodiments may be applied to a facility that performs proton-beam cancer treatment. Further, the above-described embodiments may be applied to a facility that performs treatment under BNCT (Boron Neutron Capture Therapy).

That is, the irradiator configured to radiate the particle beam may not only irradiate a patient with the particle beam but may also irradiate a predetermined target with the particle beam so as to generate neutrons.

When the main building 15 is newly constructed, the specific portion 34 is provided on the shielding wall 23 of the main building 15 in the above-described embodiments. However, when the additional building 31 is constructed, another specific portion 34 may be newly provided on the additional shielding wall 32 of the additional building 31. In this case, when one more additional building is constructed after that, the specific portion 34 of the existing additional building 31 may be opened.

When the main building 15 is newly constructed, the additional building 31 does not exist and only its extension site 30 is secured in the above-described embodiments. However, another aspect may be adopted. For example, when the main building 15 is newly constructed, only the shielding wall 32 of the additional building 31 may be built together and the specific portion 34 may be closed with the blocking portion 35. In this case, after the extension work is performed several years after the start of operation such that the equipment such as the rotating gantry 5 is added to the additional building 31, the specific portion 34 may be opened by removing the blocking portion 35.

According to at least one embodiment described above, the specific portion capable of forming the additional opening portion of the irradiation room is provided, and thus, the operating rate can be improved by shortening the period during which the treatment is interrupted at the time of the construction work.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:
1. A particle beam therapy system comprising:
   a circular accelerator configured to accelerate charged particles;
   a beam transportation line configured to lead the charged particles accelerated by the circular accelerator to an irradiation room;
   a shielding wall that is disposed around a radiation controlled area and shields radiation to be generated from the circular accelerator and the beam transportation line, the radiation controlled area being an area where the circular accelerator and the beam transportation line are disposed;
   a portion that is provided at a position that separates the radiation controlled area from outside of the shielding wall and being able to form an additional opening portion of the irradiation room;
   a blocking portion configured to close the portion and shield radiation passing through the portion; and
   an interlock configured to stop an operation of the circular accelerator when a closed state of the blocking portion changes.

2. The particle beam therapy system according to claim 1, wherein, as seen in a plan view, the portion is disposed at a position which is opposite to a region where a center of the circular accelerator is located with respect to a centroid of the radiation controlled area.

3. The particle beam therapy system according to claim 1, wherein:
the beam transportation line is composed of a main transportation line extending from the circular accelerator and a sub-transportation line extending from the main transportation line to the irradiation room; and
the portion is disposed at a position including an intersection of the shielding wall and a virtual line obtained by extending the main transportation line downstream in a transportation direction.

4. The particle beam therapy system according to claim 1, wherein, in the shielding wall, the portion is disposed at a position that separates the radiation controlled area from an extension site of the irradiation room.

5. The particle beam therapy system according to claim 1, wherein opening dimension of the additional opening portion is 1 m or less.

6. The particle beam therapy system according to claim 1, further comprising:
a branching vacuum duct that is disposed at a part closest to the portion in the beam transportation line and branches in two directions; and
a connection portion that is provided at one end of the branching vacuum duct and is connectable to an additional vacuum duct.

7. The particle beam therapy system according to claim 1, wherein:
the portion is an opening portion penetrating the shielding wall; and
the blocking portion is a shielding door that shields the radiation.

8. The particle beam therapy system according to claim 1, wherein:
the portion is an opening portion penetrating the shielding wall; and
the blocking portion is a shielding block that shields the radiation and is attachable to and detachable from the portion.

9. The particle beam therapy system according to claim 1, wherein the blocking portion is a part that forms part of the shielding wall and is lower in strength than other parts of the shielding wall.

10. The particle beam therapy system according to claim 1, further comprising a rotating gantry that is to be provided in the irradiation room and can change an irradiation direction of the charged particles having been led by the beam transportation line with respect to a subject.

11. The particle beam therapy system according to claim 1, further comprising a floor reference portion to be provided on an outer surface of the shielding wall and configured to indicate height position of a floor surface of a floor to where the portion is located.

12. A particle beam therapy system construction method comprising steps of:
providing a circular accelerator configured to accelerate charged particles at a time of newly constructing a particle beam therapy system;
constructing a beam transportation line configured to lead the charged particles accelerated by the circular accelerator to an irradiation room, at the time of newly constructing a particle beam therapy system;
constructing a shielding wall around a radiation controlled area at the time of newly constructing a particle beam therapy system, the shielding wall being configured to shield radiation to be generated from the circular accelerator and the beam transportation line, the radiation controlled area being an area in which the circular accelerator and the beam transportation line are disposed;
providing a portion at the time of newly constructing a particle beam therapy system at a position that separates the radiation controlled area from outside of the shielding wall, the portion being able to form an additional opening portion of the irradiation room;
providing a blocking portion at the time of newly constructing a particle beam therapy system, the blocking portion being configured to close the portion and block radiation having passed through the portion; and
interlocking to stop an operation of the circular accelerator when a closed state of the blocking portion changes.

13. The particle beam therapy system construction method according to claim 12, further comprising steps of:
constructing an additional shielding wall around the portion at a time of additionally constructing the particle beam therapy system;
constructing an additional beam transportation line at the time of additionally constructing the particle beam therapy system, the additional beam transportation line being configured to lead the charged particles to an irradiation room to be additionally constructed;
opening the portion by removing the blocking portion at the time of additionally constructing the particle beam therapy system; and
connecting the beam transportation line to the additional beam transportation line via the portion at the time of additionally constructing the particle beam therapy system.

14. A particle beam therapy system comprising:
a circular accelerator configured to accelerate charged particles;
a beam transportation line configured to lead the charged particles accelerated by the circular accelerator to an irradiation room;
a shielding wall that is disposed around a radiation controlled area and shields radiation to be generated from the circular accelerator and the beam transportation line, the radiation controlled area being an area where the circular accelerator and the beam transportation line are disposed;
a portion that is provided at a position that separates the radiation controlled area from outside of the shielding wall and being able to form an additional opening portion of the irradiation room; and
a blocking portion configured to close the portion and shield radiation passing through the portion;
an operation unit that can open the blocking portion only from a side of the radiation controlled area.

* * * * *